(12) United States Patent
Rydenstam

(10) Patent No.: US 8,303,563 B2
(45) Date of Patent: Nov. 6, 2012

(54) ABSORBENT ARTICLE WITH DISTINCTIVE SHEET UNDERNEATH BACKSHEET

(75) Inventor: Agneta Rydenstam, Sävedalen (SE)

(73) Assignee: SCA Hygiene Products AB, Göteborg (SE)

( * ) Notice: Subject to any disclaimer, the term of this patent is extended or adjusted under 35 U.S.C. 154(b) by 1058 days.

(21) Appl. No.: 10/904,359

(22) Filed: Nov. 5, 2004

(65) Prior Publication Data
US 2005/0113779 A1    May 26, 2005

Related U.S. Application Data

(60) Provisional application No. 60/523,312, filed on Nov. 20, 2003.

(51) Int. Cl.
*A61F 13/15* (2006.01)
*A61F 13/20* (2006.01)

(52) U.S. Cl. ...................................... 604/387

(58) Field of Classification Search ........ 604/385.03–385.04, 385.01, 385.201, 604/358, 386, 387, 389, 397, 398, 402
See application file for complete search history.

(56) References Cited

U.S. PATENT DOCUMENTS

| | | | |
|---|---|---|---|
| 4,900,320 A * | 2/1990 | McCoy | 604/387 |
| 5,221,275 A * | 6/1993 | Van Iten | 604/387 |
| 5,281,209 A * | 1/1994 | Osborn et al. | 604/385.04 |
| 5,429,633 A | 7/1995 | Davis et al. | |
| 5,460,624 A | 10/1995 | Ahr et al. | |
| 5,643,245 A | 7/1997 | Osborn, III et al. | |
| 5,649,917 A * | 7/1997 | Roberts et al. | 604/385.04 |
| 5,704,928 A | 1/1998 | Morita et al. | |
| 5,772,648 A | 6/1998 | Osborn, III et al. | |
| 6,280,428 B1 * | 8/2001 | Lash et al. | 604/385.04 |
| 6,586,654 B2 * | 7/2003 | Drevik | 604/378 |
| 6,632,208 B1 | 10/2003 | Mizutani | |
| 6,840,930 B1 | 1/2005 | Miyamoto et al. | |
| 2003/0004484 A1 * | 1/2003 | Hammons et al. | 604/385.04 |

FOREIGN PATENT DOCUMENTS

DE    43 35 443 A1    4/1995

(Continued)

OTHER PUBLICATIONS

International Preliminary Examination Report issued in a corresponding PCT application.
An English Translation of the Office Action dated Nov. 26, 2010, issued in the corresponding Colombian Patent Application No. 06046684.

*Primary Examiner* — Melanie Hand
(74) *Attorney, Agent, or Firm* — Buchanan Ingersoll & Rooney PC

(57) ABSTRACT

An absorbent article such as a sanitary napkin, a panty-liner, or an incontinence guard for light incontinence, includes a cover sheet (15) and a backsheet (12). The absorbent article (1) includes a separate sheet (4) secured on that side of the backsheet (12) facing away from a user during use of the absorbent article (1). The separate sheet (4) is preferably divided into two short end portions (7) and an intermediate portion (8) extending between the short end portions. The short end portions (7) are permanently or releasably secured via securing members (11) at a respective end portion (19) in such a way that the intermediate portion (8) forms a laterally extending through-passage (22) against the backsheet (12). The separate sheet (4) is equipped with wings (9) along at least part of the side edges (6) of the separate sheet (4).

16 Claims, 4 Drawing Sheets

FOREIGN PATENT DOCUMENTS

| | | |
|---|---|---|
| EP | 283 200 | 9/1988 |
| EP | 0 571 981 A1 | 12/1993 |
| WO | 94/02092 A1 | 2/1994 |
| WO | 94/10956 | 5/1994 |

* cited by examiner

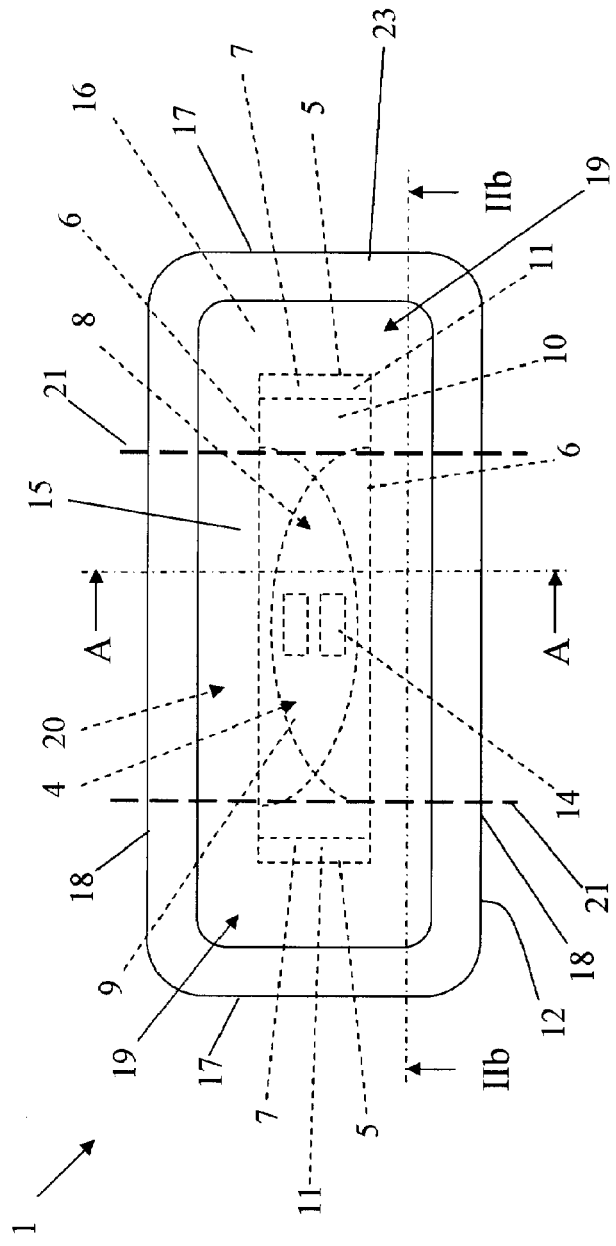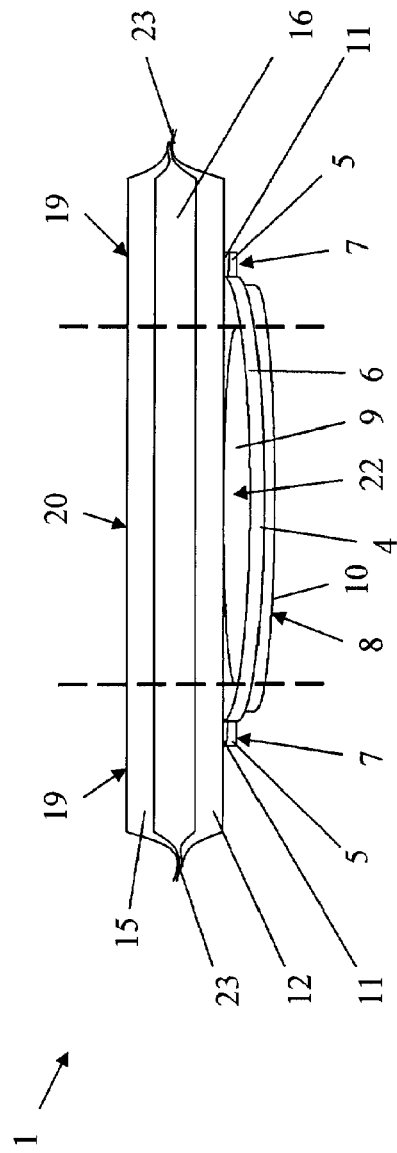

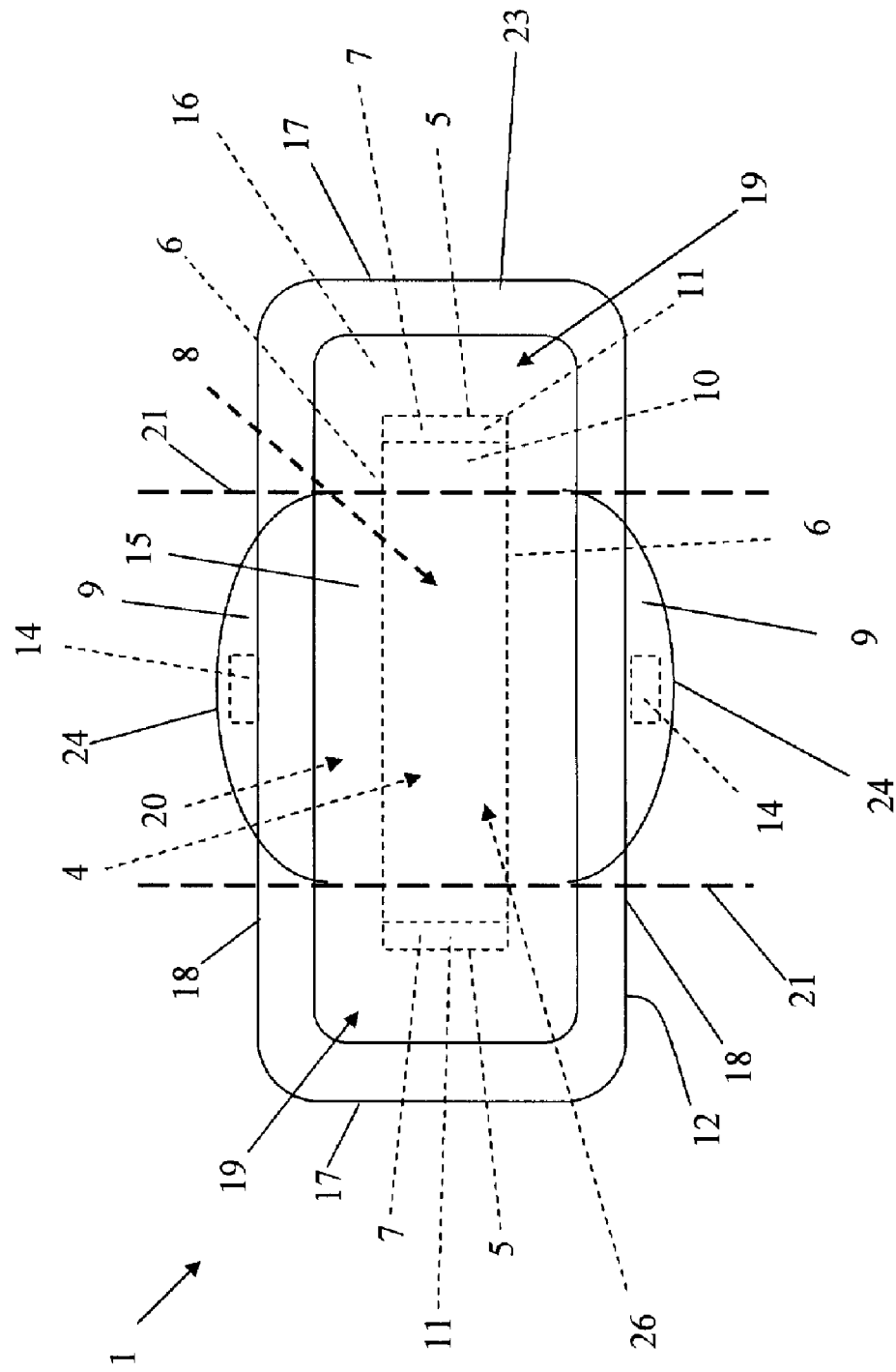

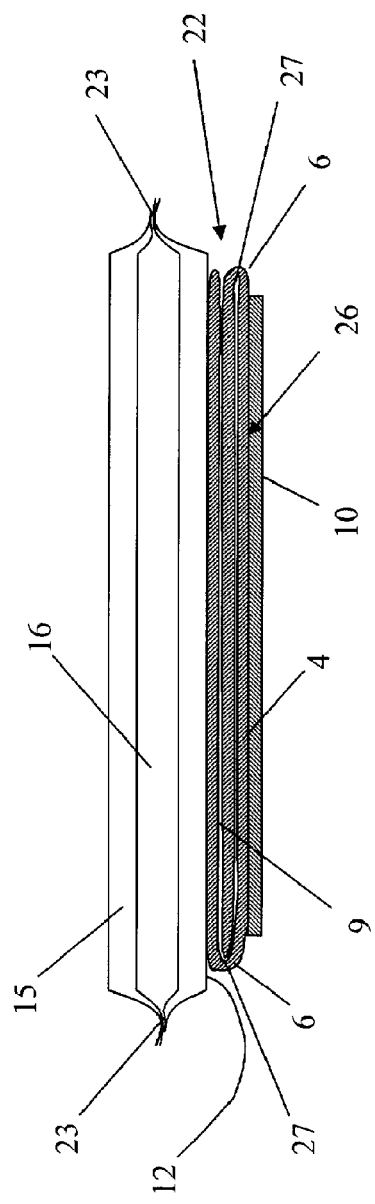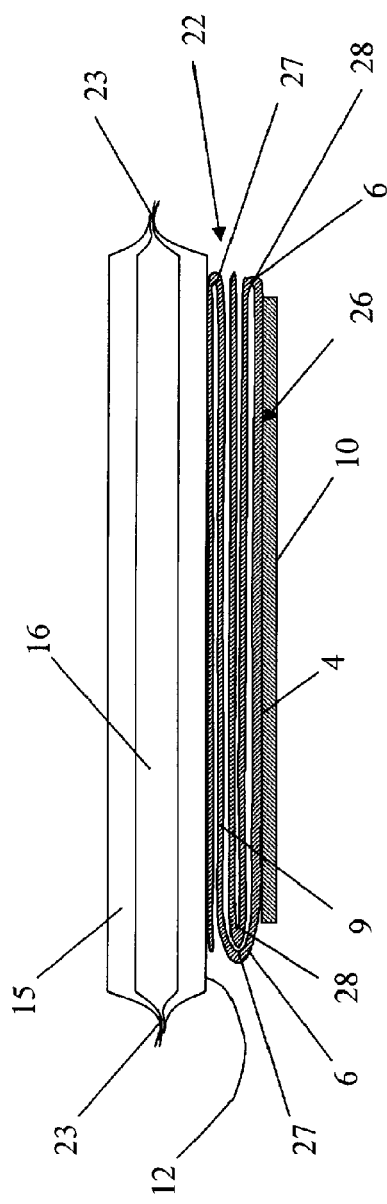

ABSORBENT ARTICLE WITH DISTINCTIVE SHEET UNDERNEATH BACKSHEET

CROSS-REFERENCE TO RELATED APPLICATIONS

The present application claims the benefit of U.S. Provisional Application No. 60/523,312, filed in the United States on Nov. 20, 2003, the entire contents of which are hereby incorporated herein by reference.

TECHNICAL FIELD

The present invention relates to an absorbent article such as a sanitary napkin, a panty-liner, or an incontinence guard for light incontinence, the absorbent article comprising a cover sheet and a backsheet. The absorbent article has a longitudinal extent between two short sides, and a lateral extent between two long sides, and is divided in the longitudinal direction into two end portions and a central portion extending between these. The absorbent article comprises a separate sheet with an extent in the longitudinal direction between two end edges and an extent in the lateral direction between two side edges. The separate sheet is secured on that side of the backsheet facing away from a user during use of the absorbent article.

BACKGROUND ART

When using absorbent articles such as sanitary napkins, panty-liners, and incontinence guards for light incontinence, the absorbent article should be designed in such a way that the article is comfortable to wear and provides the best possible protection for items of clothing. When a user moves about, the briefs and the absorbent article change position, which can cause the absorbent article to slip into an incorrect position and/or crumple together, if the article is not correctly configured.

A great many techniques are known for solving the problem of getting the absorbent article to remain in position when the user moves. By way of example, reference may be made to U.S. Pat. No. 5,772,648, in which so-called wings are used together with an adhesive sheet bearing against the briefs. The aim is to secure the absorbent article on the briefs in order, in this way, to ensure that the absorbent article remains in position relative to the briefs. Each wing includes a tab of bendable material which is secured to a separate sheet.

The separate sheet is secured on the backsheet of the absorbent article via securing members along a longitudinal, centrally located securing line which extends the entire length of the separate sheet. The wings can be folded in between the backsheet and those parts of the separate sheet which are not secured to the backsheet. Upon use, the wings can be removed from the folded-up position and thereafter folded around the briefs in order thereby to lock the absorbent article to the briefs. The separate sheet has an adhesive sheet on that side of the separate sheet which, during use, faces towards the briefs, and, during use, the adhesive sheet adheres to the briefs and additionally locks the absorbent article to the briefs.

A problem with the absorbent article according to U.S. Pat. No. 5,772,648 is that the whole of the separate sheet is fixed along the backsheet of the absorbent article, which means that the space formed between the separate sheet and the backsheet includes shallow longitudinal pockets in which the wings can be tucked. To make room, the wings have to be folded in two several times to make room in the pockets. This gives rise to an undesired thickness on the backside of the article on both sides of the longitudinal securing lines of the separate sheet. In those cases where the absorbent article is used with the wings in the folded-up position, the absorbent article can be felt to be uncomfortable on account of the thickness. In addition, the thickened side portions can cause the thinner part of the absorbent article placed between the thickened side portions to collapse, on account of the differences in thickness, when the absorbent article is exposed to pressure from outside, i.e., during use. If the wings were to be made small enough to have room in the pockets without being folded, they would not be large enough to be able to be folded around the briefs in a satisfactory manner.

Another problem when the whole of the separate sheet is secured is the fact that the separate sheet can be considered to constitute a part of the backsheet since the separate sheet directly transfers movements to the backsheet via the longitudinal securing members. When the wings are folded around the briefs during use, and when the adhesive sheet bears against the briefs, the separate sheet and also the absorbent article are held in place against the briefs, which means that movements from the briefs are transmitted directly to the absorbent article. The movements of the briefs often differ from the movement of the lower abdomen when the user moves, for which reason a direct transfer from briefs to absorbent article can give rise to the absorbent article moving with the briefs out of position from the intended position against the user's lower abdomen. If the briefs move out of position, this reduces the ability of the article to absorb the body fluids it is intended to absorb, for which reason the protective effect the absorbent article is intended to provide is not obtained to a satisfactory extent.

There is therefore a need for an absorbent article which has an improved capacity to keep the absorbent article in position relative to the user and which at the same time is comfortable, reliable and easy to use.

OBJECTS AND SUMMARY

The present invention is aimed at solving the problems, indicated above, in previously known absorbent articles such as sanitary napkins, panty-liners, and incontinence guards for light incontinence. The absorbent article comprises a cover sheet and a backsheet. The absorbent article has a longitudinal extent between two short sides, and a lateral extent between two long sides. In the longitudinal direction, the absorbent article is divided into two end regions or portions and a central portion extending between these. The absorbent article also comprises a separate sheet arranged on that side of the backsheet facing away from a user during use of the absorbent article.

The division of the article into portions or zones should not be regarded as constituting discrete boundaries, but instead as an adaptable transition between the different portions of the article. The central portion, for example, is intended to signify a part of the absorbent article which, during use, is intended to comprise the so-called wetting point. The wetting point is understood as that part of the article which is intended to bear against the user's genitals and which will receive the first liquid upon excretion of liquid. The central portion is often narrower than the front portion in order to adapt to the user's body. A large number of absorbent articles of different designs are already known, and a few examples of different designs of an absorbent article will be described in connection with the embodiments described below.

According to a preferred embodiment of the invention, the separate sheet has a longitudinal extent between two end edges and a lateral extent between two side edges, the separate sheet being divided in the longitudinal direction into two short end portions and an intermediate portion extending between these. The short end portions of the separate sheet are permanently or releasably secured via securing members at a respective end portion in such a way that the intermediate portion forms a laterally extending through-passage against the backsheet. The separate sheet is also equipped with wings along at least part of the side edges on the intermediate portion.

During use, the wings can be in a folded-in position tucked into the passage, or alternatively in a deployed position, folded around a pair of briefs.

The wings can include separate sheets secured on the separate sheet. Alternatively, the wings can constitute part of the separate sheet, i.e., the separate sheet has a design which includes the wings.

The wings can additionally include an at least partly plastically deformable material which stretches under a tensile stress and is deformed plastically and thus forms the shape of the wings. The plastically deformable wings, in their original form, can be situated in a folded-in position, i.e., they can be tucked into the passage, but they can also include a slight bulge on the respective long sides of the separate sheet. The wings can also be formed by all or part of the separate sheet consisting of a completely or partly plastically deformable material, the wings in this case being formed by plastic deformation when the separate sheet is exposed to a tensile stress. Here, tensile stress signifies a state in which the plastically deformable material is exposed to a stress by the user, i.e., when the user pulls the sheet of material in a certain direction. Here, therefore, a user can himself or herself determine the shape of the wings, by pulling to different extents and in different directions. When the wings are only partly plastically deformable, the material can be made resilient, i.e., the material seeks to recover its original shape.

The wings can additionally be equipped with grippable tabs which make it easier for the user to pull the wings out from their original position, i.e., the tabs can be used to pull the folded-in wings out from the passage or to pull a sheet of material in such a way that the sheet of material is plastically deformed to give the wings.

The advantage of the invention lies in the fact that the separate sheet gives the rest of the absorbent article a mobility, essentially in the lateral direction relative to the briefs, while at the same time the separate sheet secures the absorbent article in a position in the longitudinal direction in the briefs. A user is thus given an absorbent article which sits securely against the lower abdomen even when the briefs and the lower abdomen move in different directions.

A further advantage of the invention lies in the fact that the deployable and fold-in wings can be folded up and tucked into the passage by a distance which corresponds to the full extent of the separate sheet in the lateral direction, i.e., the full depth of the passage. This means that the wings only need to be folded once or a few times in order to be tucked away. The small number of folds gives a thin product which is comfortable and discreet for the user. A further advantage of the invention lies in the fact that the wings, when folded into the passage, can overlap one another in the form of two overlapping sheets, this giving an optimum distribution of the material which is folded into the passage across the entire surface constituted by the extent of the passage, i.e., the extent of the intermediate portion.

The separate sheet preferably has a longitudinal extent corresponding to one quarter to one third of the longitudinal extent of the absorbent article. The separate sheet can of course have an extent which corresponds to the full extent of the absorbent article, or to less than one quarter of this extent, on condition that the separate sheet can give the relative mobility with respect to the briefs that a user wishes, without compromising the secureness in the longitudinal direction. The short end portions of the separate sheet can thus be placed on the end portions of the central portion, or near the short sides, or somewhere in between.

The permanent securing members which fix the separate sheet to the backsheet can include glue or other adhesive, but the securing members can also include a seam formed by welding, for example by ultrasound or heat. The releasable securing members can include glue, adhesive, velcro, or other similar arrangements.

In a first embodiment of the invention, the wings are arranged on the separate sheet along a distance which coincides with the longitudinal extent of the central portion.

In a second embodiment of the invention, the wings are arranged on the separate sheet along a distance which exceeds the longitudinal extent of the central portion.

In a third embodiment of the invention, the wings are arranged on the separate sheet along a distance which is less than the longitudinal extent of the central portion.

The wings according to the first, second and third embodiments are not limited in the longitudinal direction by the extent of the separate sheet in the longitudinal direction, but have a maximum extent which is limited by the extent of the intermediate portion in the longitudinal direction.

In a fourth embodiment of the invention, the separate sheet is equipped with an adhesive sheet on that side of the separate sheet intended to bear against the briefs during use.

The advantage of an adhesive sheet is that the absorbent article can be used on briefs without using the wings. The securing effect is of course not as good as when using the wings and the adhesive sheet together, but it can provide sufficient securing in cases when the user does not wish to show the wings, e.g., when wearing a bikini. The abovementioned advantage of the relative mobility is also achieved when the wings are not used.

The adhesive sheet preferably includes a securing means in the form of glue, but it can also include a mechanical securing means such as velcro, press-studs, friction coatings, clip means or similar. The adhesive can be applied in one or more strands or in some other pattern. Alternatively, the whole of the underside of the separate sheet may be coated with glue. In previously known absorbent articles, the adhesive sheet is applied directly on the backsheet. The backsheet is advantageously breathable, and an adhesive sheet on the backsheet has a negative effect on this breathable quality. It is therefore an advantage to apply the adhesive sheet on the separate sheet according to the present invention, since then the breathable quality of the backsheet is not reduced to the same great extent as in the previously known articles.

A protective sheet is advantageously applied on the adhesive sheet. The protective sheet is preferably a silicone-treated paper, but other types of protective sheet are of course also possible, for example, waxed paper, stamped or release-agent-treated plastic film, textile strips to attach to Velcro, or the like.

In a fifth embodiment of the invention, each wing in the folded-in position is folded in two. In this embodiment, the wings, when folded in two, can also lie overlapping one another. The advantage of this is that, in the deployed position, the wings folded in two have a greater extent than those wings which are intended to be folded in and overlap without being folded in two.

In a sixth embodiment of the invention, the wings comprise securing members intended to be secured to the briefs when the wings are in the deployed position, i.e., the securing members are to be fixed to the outside of the briefs when the wings have been folded over the edges of the briefs. The advantage of such securing members is that the wings remain in the folded-over position, the separate sheet being held in place in a reliable manner against the briefs.

The absorbent article can also comprise an absorption body placed between the cover sheet and the backsheet. The absorption body is made of one or more liquid-absorbing materials and can be made up of one or more layers of identical or different materials, or of different mixtures present in the absorption body. The absorption body is preferably produced from one or more layers of cellulose pulp. The pulp can originally be in the form of rolls, bales or sheets which, in the production of the sanitary napkin, are dry-defibred and converted in fluffed form to a pulp mat, sometimes with admixture of what are called superabsorbents, namely polymers with the capacity to absorb several times their own weight of water or body fluid. An alternative to this is to dry-shape a pulp mat as is described in WO 94/10956. Examples of other absorption materials that can be used are various types of natural fibres such as cotton fibres, peat, or similar. It is of course also possible to use absorbent synthetic fibres, or particles of a high-absorbency polymer material of the type which on absorption chemically binds large quantities of liquid, with formation of a liquid-containing gel, or to use mixtures of natural fibres and synthetic fibres. The absorption body can also contain other components, such as shape-stabilizing means, liquid-spreading means, or binders such as thermoplastic fibres which have been heat-treated in order to hold short fibres and particles together in a coherent unit. It is also possible to use different types of absorbent foam material in the absorption body.

The cover sheet is advantageously made of a skin-friendly material and, when an absorption body is used, the cover sheet is liquid-permeable.

The cover sheet is made of one or more liquid-permeable materials and can be made up of one or more layers of identical or different materials, or different material mixtures present in the sheet. The cover sheet can be of any conventional material, for example nonwoven fibre material, perforated plastic film, or a laminate of a perforated plastic film and a nonwoven.

In those cases where the absorbent article comprises only a cover sheet and a backsheet, the cover sheet can be made completely or partially of such an absorption material which can constitute the abovementioned absorption body.

The backsheet is made up of one or more layers of a liquid-impermeable material. The backsheet can be made up of one or more layers of identical or different materials, or of different mixtures present in the backsheet. Thin, liquid-tight plastic films are suitable for the purpose, but it is also possible to use material which is liquid-permeable to start with but which has been provided with a coating of plastic, resin, or other liquid-tight material. The backsheet can therefore include any material which satisfies the criterion of liquid-impermeability and has sufficient flexibility and skin-friendliness for the purpose. Examples of materials which are suitable as barrier sheets are plastic films, nonwovens, and laminates thereof. The plastic film can, for example, be of polyethylene, polypropylene or polyester. The backsheet can alternatively include a laminate of a liquid-impermeable plastic sheet, facing towards the absorption body, and a nonwoven, facing towards the user's underwear. Such a construction provides a leaktight barrier sheet with a textile feel. The liquid-blocking backsheet can also be made of a breathable material. A breathable backsheet of this kind can, for example, be made of what is called SMS (spunbond-meltblown-spunbond) or a breathable plastic film consisting of polyethylene. A plastic film of this kind is described in EP 283 200.

The separate sheet includes one or more materials, for example nonwoven, plastic film, cloth, lace, or the like. The separate sheet can additionally include one or more sheets, laminates, of different mixtures of material. The material is advantageously bendable and can be completely or partially transparent and can additionally be of any desired color or completely colorless. As has been mentioned earlier, the separate sheet can additionally be stretchable and/or completely or partially plastically deformable.

The backsheet and the separate sheet are advantageously made in such a way that the contact surfaces between the two sheets have low friction. This is to be understood as meaning that the separate sheet slides easily on the backsheet. This can be achieved by treating the backsheet and/or the separate sheet in such a way that it has a smooth surface.

BRIEF DESCRIPTION OF THE FIGURES

The invention will be described below with reference to a number of figures, where:

FIG. 2a is a diagrammatic illustration showing a top view of an absorbent article according to FIG. 1, with the wings folded in;

FIG. 2b is a diagrammatic illustration showing a side view in cross section along IIb-IIb in FIG. 2a;

FIG. 3 is a diagrammatic illustration showing a top view of an absorbent article according to FIG. 2a with the wings deployed;

FIG. 4a is a diagrammatic illustration showing a side view in cross section A-A in FIG. 2, and FIG. 4b is a diagrammatic illustration showing a side view in cross section A-A, but according to a second embodiment of the invention.

DETAILED DESCRIPTION OF THE PREFERRED EMBODIMENTS

Figure 1:
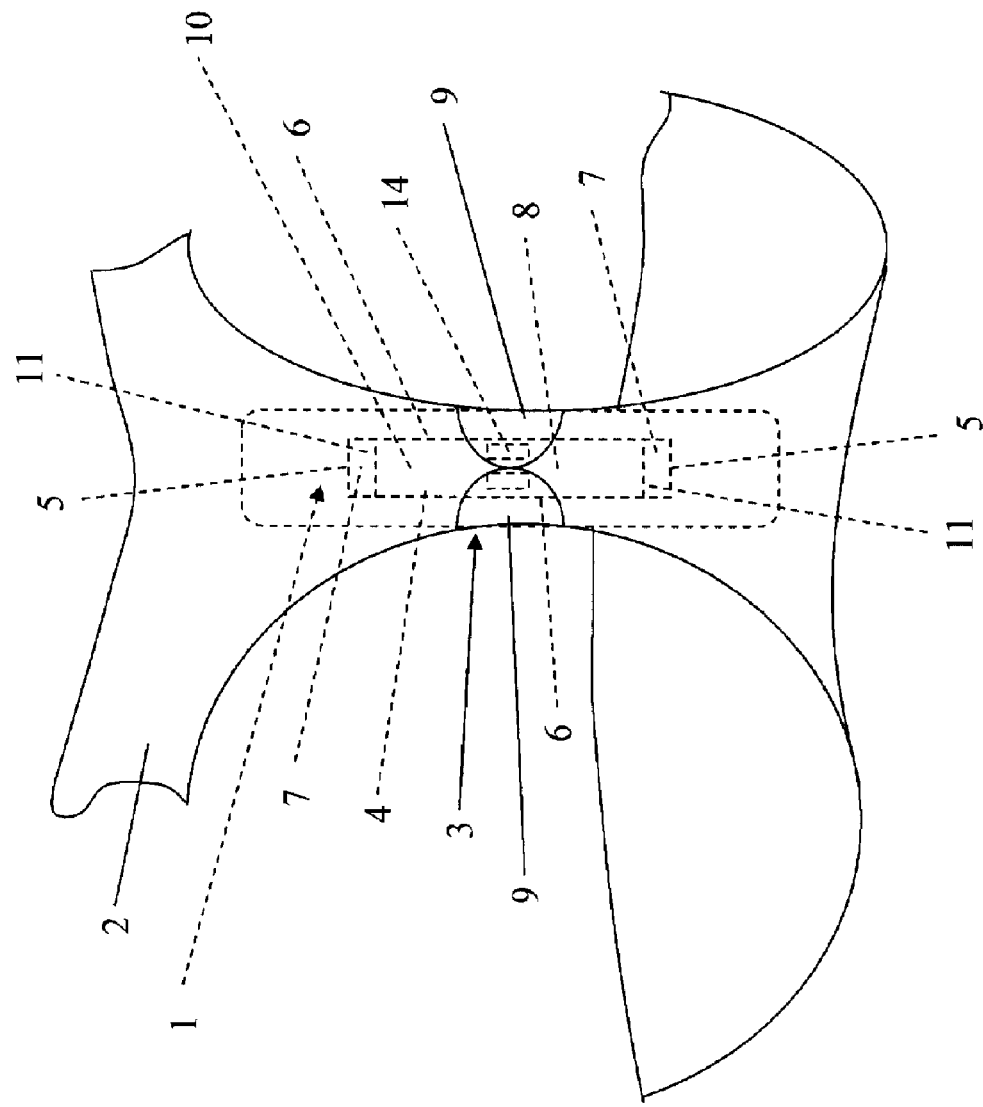
FIG. 1 is a diagrammatic illustration showing an absorbent article according to one embodiment of the invention, arranged in a pair of briefs.

FIG. 1 is a diagrammatic illustration of an absorbent article 1 according to one embodiment of the invention, arranged in a pair of briefs 2. The absorbent article 1 is secured in the central portion 3 of the briefs 2, which central portion 3 is intended to lie against a user's lower abdomen during use. The absorbent article 1 comprises a separate sheet 4 with a longitudinal extent between two end edges 5, and a lateral extent between two side edges 6. In the longitudinal direction, the separate sheet 4 is divided into two short end portions 7 and an intermediate portion 8 extending between these.

The separate sheet 4 is equipped with wings 9 and an adhesive sheet 10. The end portions 7 of the separate sheet 4 are in each case secured via securing members 11 to a backsheet 12 belonging to the absorbent article 1. FIG. 1 shows that the wings 9 are folded around the edges 13 at the central portion 3 of the briefs in such a way that the wings 9 hold the separate sheet 4 against the central portion 3 of the briefs 2. The wings 9 are additionally equipped with securing members 14 which secure them to the material of the briefs 2 in such a way that the folding of the wings 9 around the central portion 3 is maintained. The adhesive sheet 10 bears against the central portion 3 of the briefs 2 for the purpose of further securing the separate sheet 4 to the briefs 2.

FIG. 2a is a diagrammatic top view of the absorbent article according to FIG. 1. In addition to the backsheet 12, the absorbent article also comprises a cover sheet 15 and, between these, an absorption body 16. The absorbent article 1 has a longitudinal extent between two short sides 17, and a lateral extent between two long sides 18. In the longitudinal direction, the absorbent article 1 is divided into two end portions 19 and a central portion 20 extending between these, i.e., into three zones.

The division of the absorbent article 1 into three zones is intended to simplify the description of the invention. The three zones are marked by two parallel broken lines 21 which run at right angles to an imagined longitudinal center line of the article. In FIG. 2a, the absorbent article 1 is shown with a rectangular shape. In another embodiment, the absorbent article can be given a different shape, for example an hourglass shape, triangular shape, parallel trapezoidal shape, asymmetrical shape, or some other shape deemed suitable in absorbent articles 1 of the type to which the present invention relates. The absorbent article can additionally comprise an absorption body with divided rear portion and/or cup-shaped front portion. The absorbent article can additionally be designed with a raised area on at least parts of the central portion. The raised area is intended to bear against a user's genitals for optimum fit.

FIG. 2a shows that the separate sheet 4 extends from one end region or portion 19 and across the central portion 20 to the other end region or portion 19. The short end portions 7 of the separate sheet 4 are permanently or releasably secured by securing members 11 to the respective end region 19 in such a way that the intermediate portion 8 forms a through-passage 22 against the backsheet 4. The separate sheet 4 is equipped with wings 9 applied along at least parts of the side edges 6 on the intermediate portion 8. FIG. 2a shows that the wings 9 are arranged on the separate sheet 4 along a distance which coincides with the central portion 20 of the absorbent article 1. In another embodiment, the wings 9 can of course be arranged on the side edges 6 of the separate sheet 4 along a distance which is longer or shorter than the distance constituted by the central portion 20 of the absorbent article 1. For example, the wings 9 can extend the entire distance between the two short end portions 7 of the separate sheet.

FIG. 2a shows the article 1 with the wings 9 folded into the through-passage 22, but, by means of a simple maneuver, the wings 9 can be withdrawn from the through-passage 22 and then folded around the central portion 3 of the briefs 2 in accordance with FIG. 1. It is not necessary to use the wings 9 during use of the absorbent article 1, and instead it is possible to choose between having the wings 9 tucked into the passage 22 or having them in the deployed position folded around a pair of briefs 2. If the wings 9 are not used, the adhesive sheet 10 can constitute the sole zone of attachment to the briefs 2. Such a situation may arise, for example, when a user does not wish the wings 9 to show outside the briefs 2, for example when wearing bikini briefs.

Since the separate sheet 4 is secured only via the short end portions 7 at a respective end portion 19 of the article, the intermediate portion 8 constitutes a unit which is not directly coupled to the backsheet 12, and this means that the intermediate portion 8 can move without the backsheet 12 being forced to follow this movement. An advantage of such an arrangement is that the separate sheet 4 secured to the briefs 2 can follow the movement of the briefs 2 without other parts (cover sheet, absorption body, backsheet) of the absorbent article 1 following each movement of the briefs 2. The free mobility between the separate sheet 1 and the other parts of the absorbent article permits a certain free mobility in the longitudinal direction, but mainly in the lateral direction. The free mobility provides increased security of the absorbent article, since the briefs 2 and the separate sheet 4 are allowed to move out of position relative to a user's lower abdomen, without the other parts of the absorbent article 1 shifting from position.

Irrespective of whether the wings 9 are used together with the adhesive sheet 10 or not, the advantage is obtained that the separate sheet 4 moves with the briefs 4, and the rest of the absorbent article 1 with the user's lower abdomen.

FIG. 2a also shows a peripheral edge part 23 which binds the cover sheet 15 to the backsheet 12. The edge part 23 can be obtained, for example, by welding, gluing, or some other joining method suitable for the purpose. The edge part 23 can additionally comprise parts of the absorbent article, which is shown for example in FIG. 2b. An absorbent article 1 according to the invention does not need to have an edge part 23 according to FIG. 2a, and instead the edge part can be formed, for example, by the backsheet 12 being folded across the side edges of the absorbent article and secured on the cover sheet 15.

FIG. 2b is a diagrammatic side view in cross section IIb-IIb in FIG. 2a, where the absorbent article 1 is made up of the cover sheet 15, the backsheet 12 and the absorption body 16 located between these. FIG. 2b shows the two parallel broken lines 21 which delimit the three zones forming the two end portions 19 and the central portion 20 located between these. In FIG. 2b, the short end portions 7 of the separate sheet 4 are secured to the backsheet 12 approximately at the middle of the respective end portion 19. In another embodiment, the short end portions 7 can be secured to the backsheet 12 at any desired position within the respective end portion 19. The positioning of the short end portions 7 can depend, for example, on the configuration of the wings or on the shape of the rest of the absorbent article 1. The size of the short end portions 7 depends on their positioning and on what type of securing arrangements 11 are used. FIG. 2b shows the through-passage 22 into which the wings are folded between the separate sheet 4 and the backsheet 12.

FIG. 3 is a diagrammatic top view of an absorbent article 1 according to FIG. 2a, with the wings 9 deployed. The wings 9 have a semicircular shape along the outer edge parts 24 of the wings, but a base which has an extent from end portion 19 to end portion 19 along the side edges 6 of the separate sheet 4. The wings 9 constitute a part of the separate sheet 4, for example by means of the wings 9 and the rectangular main part 26 of the separate sheet 4 being cut or punched, or produced in some other way, from the same blank. Alternatively, the wings 9 can be secured to the rectangular main part 26, for example by welding, gluing, or another suitable method.

The wings 9 do not have to be semicircular in shape, and instead can have a triangular shape, rectangular shape, quadratic shape, parallel trapezoidal shape, hourglass shape, asymmetrical shape, or another suitable shape. As has been mentioned earlier, the wings 9 can additionally be made of a completely or partly plastically deformable material which changes shape after tensile stressing.

FIG. 4a shows a diagrammatic side view in cross section A-A from FIG. 2, where the folding-in of the wings 9 into the through-passage 22 is illustrated. The wings 9 are folded once across a first fold line 27 which coincides with the side edges 6 of the rectangular main part 26 of the separate sheet 4. The wings 9 are additionally folded to overlap in the through-passage 22. The wings 9 lie flat against one another and are evenly distributed across the backsheet 12, which minimizes the thickness of the absorbent article 1. Since the wings 9 are arranged in the absorbent article 1 in such a way as to obtain a minimal thickness of the article, advantages are afforded for example from the point of view of packaging, as more articles can be packed per packaging volume. When the user wishes to use the absorbent article without the wings, i.e., when the wings are in the folded-in position, further advantages are afforded with the thin absorbent article, because a thin article is both discreet and comfortable. By virtue of the fact that the wings 9 are evenly distributed across the backsheet 12, a product is obtained with an evenly distributed thickness, which reduces the risk of the absorbent article being deformed during use with the wings 9 in the folded-in position.

FIG. 4b is a diagrammatic side view in cross section A-A, but according to a second embodiment of the invention. Here, as in FIG. 4a, the wings 9 are folded once across a first fold line 27 which coincides with the side edges 6 of the rectangular main part 26 of the separate sheet 4. The wings 9 are additionally folded in two on themselves across a second fold line 28 which essentially coincides with the side edges 6 of the rectangular main part 26 of the separate sheet 4. The twice-folded wings 9 additionally overlap in the through-passage. An advantage of this embodiment is that the outer edge parts 24 of the wings face outwards from the through-passage, making it possible for a user to take hold of the outer edge parts 24 of the wings 9 and then pull the wings 9 out from the through-passage 22, whereupon the wings 9 folded in two deploy. The advantages mentioned in connection with FIG. 4a, in terms of even distribution and a thin article, also apply to the embodiment according to FIG. 4b.

The invention is not limited to the abovementioned embodiments and instead can be varied within the scope of the attached patent claims. For example, the wings can be folded more than twice. In addition, the wings can be provided with grippable tabs secured on the outer edge parts of the wings. The grippable tabs can be used to pull the wings out from their folded-in position. The grippable tabs can additionally be used as gripping means for a user who wishes to shape the wings from a plastically deformable sheet belonging to the separate sheet.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An absorbent article having a longitudinal direction and a lateral direction, wherein the longitudinal direction of the article is longer than the lateral direction of the article, the article comprising:
    a cover sheet;
    a backsheet;
    the absorbent article having a short side extending in the lateral direction at each longitudinal end of the article and a long side extending in the longitudinal direction at each lateral end of the article and the article having a longitudinal end region at each of the longitudinal ends of the article and a central portion extending between the two longitudinal end regions;
    a separate sheet with an extent in the longitudinal direction and an extent in the lateral direction, the separate sheet being secured on a side of the backsheet facing away from a user during use of the absorbent article, wherein the separate sheet includes two longitudinal end portions and an intermediate portion extending between the two longitudinal end portions, the separate sheet extending from one longitudinal end region to the other longitudinal end region, and the separate sheet includes two longitudinally extending edges and two laterally extending edges, and each of the longitudinal end portions is permanently or releasably secured via a securing member at a respective end region in such a way that the intermediate portion forms in combination with the backsheet a through-passage that extends in the lateral direction and has an opening at each of the longitudinally extending edges of the separate sheet; and
    the separate sheet being equipped with wings along at least part of the side edges of the separate sheet.

2. The absorbent article according to claim 1, wherein the wings include an at least partly plastically deformable material which stretches under a tensile stress and is deformed plastically and thus forms the shape of the wings.

3. The absorbent article according to claim 1, wherein the wings, during use, are adapted to be situated in a folded-in position tucked into the through-passage or in a deployed position, folded around a pair of briefs.

4. The absorbent article according to claim 1, wherein the wings are arranged on the separate sheet along a distance which coincides with the longitudinal extent of the central portion.

5. The absorbent article according to claim 1, wherein the wings are arranged on the separate sheet along a distance which exceeds the longitudinal extent of the central portion.

6. The absorbent article according to claim 1, wherein the wings are arranged on the separate sheet along a distance which is less than the longitudinal extent of the central portion.

7. The absorbent article according to claim 1, wherein the separate sheet is equipped with an adhesive sheet on that side of the separate sheet intended to bear against the briefs during use.

8. The absorbent article according to claim 1, wherein the wings, in the folded-in position, together constitute two overlapping sheets.

9. The absorbent article according to claim 1, wherein each wing in the folded-in position is folded in two.

10. The absorbent article according to claim 9, wherein the wings, when folded in two, lie overlapping one another.

11. The absorbent article according to claim 1, wherein the wings comprise securing members intended to be secured to the briefs when the wings are in the deployed position, folded around a pair of briefs.

12. The absorbent article claim 1, wherein the absorbent article comprises an absorption body between the cover sheet and the backsheet.

13. An absorbent article, comprising:
    a cover sheet;
    a backsheet;
    the absorbent article having a longitudinal extent between two short sides and a lateral extent between two long sides and the article having a longitudinal end region at each of the longitudinal ends of the article and a central portion extending between the two end regions;
    a separate sheet with an extent in the longitudinal direction and an extent in the lateral direction, the separate sheet being secured on a side of the backsheet facing away from a user during use of the absorbent article, wherein the separate sheet includes two end portions and an intermediate portion extending between the two end portions, the separate sheet extending from one longitudinal end region to the other longitudinal end region, and the separate sheet includes two longitudinally extending edges and two laterally extending edges, and each of the end portions is permanently or releasably secured via a securing member at a respective longitudinal end region in such a way that the intermediate portion forms in combination with the backsheet a through-passage that extends in the lateral direction and has an opening at each of the longitudinally extending edges of the separate sheet;

the separate sheet being equipped with wings along at least part of the side edges of the separate sheet; and adhesive is provided on a side of the separate sheet that is intended to bear against the briefs during use, wherein the adhesive is provided only in regions where the separate sheet is not directly secured to the backsheet.

14. The absorbent article according to claim 13, wherein the wings, during use, are adapted to be situated in a folded-in position tucked into the through-passage or in a deployed position, folded around a pair of briefs.

15. The absorbent article according to claim 13, wherein the wings comprise securing members intended to be secured to the briefs when the wings are in the deployed position, folded around a pair of briefs.

16. The absorbent article according to claim 13, wherein the wings include an at least partly plastically deformable material which stretches under a tensile stress and is deformed plastically and thus forms the shape of the wings.

* * * * *